(12) United States Patent
Chowdry et al.

(10) Patent No.: US 10,777,302 B2
(45) Date of Patent: Sep. 15, 2020

(54) IDENTIFYING VARIANTS OF INTEREST BY IMPUTATION

(71) Applicant: 23andMe, Inc., Mountain View, CA (US)

(72) Inventors: Arnab Chowdry, Sunnyvale, CA (US); Geoffrey Benton, Cupertino, CA (US); Brian Thomas Naughton, Mountain View, CA (US)

(73) Assignee: 23andMe, Inc., Sunnyvale, CA (US)

( * ) Notice: Subject to any disclaimer, the term of this patent is extended or adjusted under 35 U.S.C. 154(b) by 239 days.

(21) Appl. No.: 15/256,388

(22) Filed: Sep. 2, 2016

(65) Prior Publication Data

US 2017/0329901 A1 Nov. 16, 2017

Related U.S. Application Data (63) Continuation of application No. 13/908,455, filed on Jun. 3, 2013, now abandoned.

(Continued)

(51) Int. Cl.
*G16B 40/00* (2019.01)
*G16B 50/00* (2019.01)
*G16B 20/00* (2019.01)

(52) U.S. Cl.
CPC ............. *G16B 40/00* (2019.02); *G16B 20/00* (2019.02); *G16B 50/00* (2019.02)

(58) Field of Classification Search
CPC .......... G06F 19/18; G06F 19/22; G06F 19/24; G06F 19/12; G06F 19/3431; G06F 19/3443; G06F 19/363; G06F 19/10; G06F 19/20; G06F 19/34; G06F 19/3437; G06F 17/30303; G06F 17/30306; G06F 19/322; G06F 19/345; G06F 19/707; G06F 16/2462; G06F 16/288; G06F 17/18; G06F 19/00;
(Continued)

(56) References Cited

U.S. PATENT DOCUMENTS 8,655,821 B2 * 2/2014 Aliferis ................. G06N 20/00
  706/46
9,928,338 B2 * 3/2018 Tang ..................... G06F 19/34

(Continued)

FOREIGN PATENT DOCUMENTS

| WO | WO2013181256 | * | 1/2013 |
| WO | WO2017083091 | * | 1/2017 |
| WO | WO2017/083091 | * | 5/2017 |

OTHER PUBLICATIONS

Browning et al. Human Genetics (2008) vol. 124 pp. 439-450; Missing data imputation and haplotype phase inference for genome wide association studies.

(Continued)

*Primary Examiner* — Mary K Zeman
(74) *Attorney, Agent, or Firm* — Weaver Austin Villeneuve & Sampson LLP; David K. Buckingham (57) ABSTRACT

Processing genetic information comprises: receiving an input that includes information pertaining to a specific genetic variant; and identifying, in a database comprising genotype information of a plurality of candidate individuals, a matching individual imputed to have the specific genetic variant. The genotype information of the matching individual corresponding to the specific genetic variant is not directly assayed.

20 Claims, 9 Drawing Sheets

Related U.S. Application Data (60) Provisional application No. 61/689,398, filed on Jun. 4, 2012.

(58) Field of Classification Search
CPC .......... G06F 19/30; G06N 5/04; G06N 20/00; G06N 7/005; G06N 5/045; G06N 5/046; C12Q 1/6883; C12Q 2600/158; C12Q 2600/156; C12Q 1/6886; C12Q 2600/106; C12Q 2600/118; C12Q 1/68; C12Q 2600/172; G16B 40/00; G16B 30/00; G16B 20/00; G16B 50/00; G16B 10/00; G16B 25/00; G16B 20/20; G16B 40/20; G16B 50/30; G16B 5/00; G16H 50/30; G16H 50/20; G16H 10/60; G16H 50/70; G16H 50/50; G05B 23/0229
See application file for complete search history.

(56) References Cited

U.S. PATENT DOCUMENTS

| | | | | |
|---|---|---|---|---|
| 10,296,842 | B2* | 5/2019 | Lu | G06F 17/18 |
| 10,468,141 | B1* | 11/2019 | Valenzuela | G16B 20/20 |
| 2012/0053845 | A1* | 3/2012 | Bruestle | G16B 20/00 |
| | | | | 702/20 |
| 2013/0085728 | A1* | 4/2013 | Tang | G06F 19/34 |
| | | | | 703/2 |
| 2015/0106115 | A1* | 4/2015 | Hu | G16H 10/60 |
| | | | | 705/3 |
| 2015/0315645 | A1* | 11/2015 | Gaasterland | G16B 20/00 |
| | | | | 506/2 |
| 2015/0356243 | A1* | 12/2015 | Andreassen | G16B 30/00 |
| | | | | 702/20 |
| 2017/0364631 | A1* | 12/2017 | Paul | G16B 30/00 |
| 2018/0044730 | A1* | 2/2018 | Pickrell | C12Q 1/6869 |
| 2019/0348147 | A1* | 11/2019 | Kaseniit | G16B 10/00 |

OTHER PUBLICATIONS

Chanda et al. Journal of Human Genetics 2012 vol. 57 pp. 411-421: Comprehensive evaluation of imputation performance in African Americans.

Druet et al. J Dairy Science 2010 vol. 93 pp. 5443-5494; Imputation of genotypes from different single nucleotide polymorphisms in dairy cattle.

Hickey, J. M. et al. Genetics Selection Evolution (Mar. 30, 2012) vol. 44 No. 9 pp. 1-11.

Krithika et al. BMC Medical Genomics May 1, 2012 vol. 5 No. 12 pp. 1-12; Evaluation of the imputation performance of the program IMPUTE in an admixed sample from Mexico City using several model designs.

Naughton, et al., "Interpretation of Variants of Unknown Significance in a Large Database of Genotyped and Phenotyped Individuals," ASHG 2012 Annual Meeting, Nov. 2012, p. 1.

Browning, et al., "Rapid and Accurate Haplotype Phasing and Missing-Data Inference for Whole-Genome Association Studies by Use of Localized Haplotype Clustering," The American Journal of Human Genetics, vol. 81, Nov. 2007, pp. 1084-1097.

Browning, et al., "Identity by Descent Between Distant Relatives: Detection and Applications," Annu. Rev. Genet., vol. 46, Dec. 2012, pp. 617-633.

Cavalli-Sforza, L., "The Human Genome Diversity Project: past, present and future," Nature Reviews, Genetics, vol. 6, Apr. 2005, pp. 333-340.

Crawford, et al., "Evidence for substantial fine-scale variation in recombination rates across the human genome," Nature Genetics, vol. 36, No. 7, Jul. 2004, pp. 700-706.

Delaneau, et al., "A Linear complexity phasing method for thousands of genomes," Nature Methods, vol. 9, No. 2, Feb. 2012, pp. 179-184.

Fuchsberger, et al., "Minimac2: faster genotype imputation," Bioinformatics, vol. 31, No. 5, Oct. 22, 2014, pp. 782-784. <doi:10.1093/bioinformatics/btu704>.

Gusev, et al., "Whole population, genome-wide mapping of hidden relatedness," Genome Research, vol. 19, 2009, pp. 318-326.

Howie, et al., "A Flexible and Accurate Genotype Imputation Method for the Next Generation of Genome-Wide Association Studies," PLoS Genetics, vol. 5, No. 6, Jun. 2009, pp. 1-15.

Howie, et al., "Fast and accurate genotype imputation in genome-wide association studies through pre-phasing," Nature Genetics, vol. 44, No. 8, Aug. 2012, pp. 955-960.

Patterson, et al., "Population Structure and Eigenanalysis," PLoS Genetics, vol. 2, No. 12, e190, Dec. 2006, pp. 2074-2093.

Porras-Hurtado, et al., "An overview of STRUCTURE: applications, parameter settings, and supporting software," Frontiers in Genetics, vol. 4, No. 96, May 29, 2013, pp. 1-13.

Pritchard, et al., "Association Mapping in Structured Populations," Am. J. Hum. Genet., vol. 67, 2000, pp. 170-181.

Purcell, et al., "PLINK: A Tool Set for Whole-Genome Association and Population-Based Linkage Analysis," The American Journal of Human Genetics, vol. 81, Sep. 2007, pp. 559-575.

Rabiner, L., "A Tutorial on Hidden Markov Models and Selected Applications in Speech Recognition," Proceedings of the IEEE, vol. 77, No. 2, Feb. 1989, pp. 257-286.

Scheet, et al., "A Fast and Flexible Statistical Model for Large-Scale Population Genotype Data: Applications to Inferring Missing Genotypes and Haplotypic Phase," The American Journal of Human Genetics, vol. 78, Apr. 2006, pp. 629-644.

Stephens, et al., "A Comparison of Bayesian Methods for Haplotype Reconstruction from Population Genotype Data," Am. J. Hum. Genet., vol. 73, 2003, pp. 1162-1169.

Stephens, et al., "A New Statistical Method for Haplotype Reconstruction from Population Data," Am. J. Hum. Genet., vol. 68, 2001, pp. 978-989.

Stephens, et al., "Accounting for Decay of Linkage Disequilibrium in Haplotype Inference and Missing-Data Imputation," Am. J. Hum. Genet., vol. 76, 2005, pp. 449-462.

The International HapMap Consortium, "A haplotype map of the human genome," Nature, vol. 437, Oct. 27, 2005, pp. 1299-1320. <doi:10.1038/nature04226>.

The International HapMap Consortium, "A second generation human haplotype map of over 3.1 million SNPs," Nature, vol. 449, Oct. 18, 2007, pp. 851-860. <doi:10.1038/nature06258>.

* cited by examiner

```
Alice  A G T | C T G | C A A | ... | — 902
       C G A | C A G | T C A | ... | — 904

Bob    C A T | G A C | C C G | ... | — 906
       A A T | C T G | C A A | ... | — 908
```

IDENTIFYING VARIANTS OF INTEREST BY IMPUTATION

CROSS REFERENCE TO OTHER APPLICATIONS

This application is a continuation of U.S. patent application Ser. No. 13/908,455 entitled IDENTIFYING VARIANTS OF INTEREST BY IMPUTATION filed Jun. 3, 2013, which claims priority to U.S. Provisional Patent Application No. 61/689,398 entitled INTERPRETATION OF VARIANTS OF UNKNOWN SIGNIFICANCE USING IDENTITY-BY-DESCENT IN A LARGE DATABASE OF GENOTYPED AND PHENOTYPED INDIVIDUALS filed Jun. 4, 2012 which is incorporated herein by reference for all purposes.

BACKGROUND OF THE INVENTION

Genetic researchers often need to study specific genetic variants to understand their significance. For example, researchers may be interested in knowing whether a certain genetic variant of interest (VOI) (e.g., having G/C allele at location 150 on Chromosome 3) is correlated with a particular phenotype expression (e.g., having a particular disease). Currently, the interpretation of specific genetic variants and identification of cohorts with such variants, particularly variants of unknown significance (VUS) from whole-genome sequence data, pose substantial challenges in genetics studies. VUS are so named because their correlations with specific phenotypes (e.g., certain diseases) are unknown prior to the studies. VUS are often too rare to be amenable to genome-wide association studies and thus traditionally have been interpreted with reference to the primary literature (especially for high-penetrance or Mendelian mutations) or by computational methods (e.g., Sorting Intolerant From Tolerant (SIFT), PolyPhen).

Some large personal genomic information database in existence can include individuals who actually possess the genetic variants of interest (VOI). For example, 23andMe, Inc., a personal genetics service company, has accumulated a large database comprising data of over 250,000 individuals. The large databases typically employ genotype data comprising genetic markers to represent an individual's genome, instead of using full sequence data. Because the genotype data is usually obtained using chips that have specific probes assaying selective locations on the genome, the data is typically not a full sequence and the VOI is not necessarily directly assayed (for example, an individual's assayed genotype data may not include specific information about the person's allele at location 150 on Chromosome 3 because the chip used for assaying does not have a probe at that location), making it difficult to study the VOI by directly using information stored in the large databases.

BRIEF DESCRIPTION OF THE DRAWINGS

Various embodiments of the invention are disclosed in the following detailed description and the accompanying drawings.

DETAILED DESCRIPTION

The invention can be implemented in numerous ways, including as a process; an apparatus; a system; a composition of matter; a computer program product embodied on a computer readable storage medium; and/or a computer processor, such as a computer processor configured to execute instructions stored on and/or provided by a memory coupled to the computer processor. In this specification, these implementations, or any other form that the invention may take, may be referred to as techniques. In general, the order of the steps of disclosed processes may be altered within the scope of the invention. Unless stated otherwise, a component such as a computer processor or a memory described as being configured to perform a task may be implemented as a general component that is temporarily configured to perform the task at a given time or a specific component that is manufactured to perform the task. As used herein, the term 'computer processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Imputation-based processing of genetic information is described. In some embodiments, a database is used to store genotype information (and optionally other information such as phenotype information) of a plurality of candidate individuals. Although the genotype information pertaining to a specific genetic variant (also referred to as a variant of interest (VOI)) is not directly assayed (i.e., not directly tested using a genotyping chip or other genotyping platform) for all the candidate individuals, matching individuals who are deemed to have the specific genetic variant are identified using imputation techniques such as statistical imputation, Identity by Descent (IBD)-based imputation, or a combination thereof.

Figure 1:
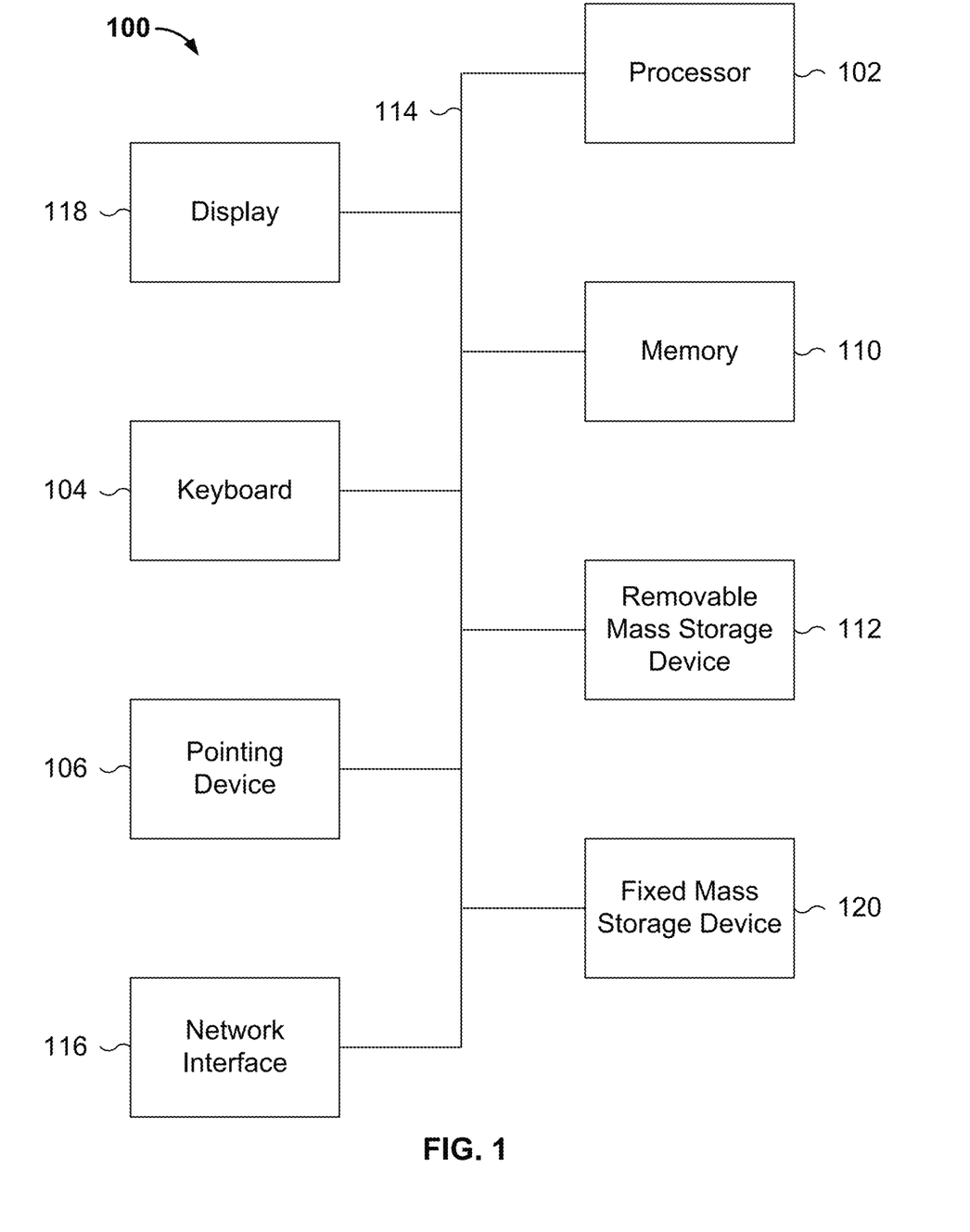
FIG. 1 is a functional diagram illustrating a programmed computer system for performing imputation-based processing of genetic information in accordance with some embodiments.

FIG. 1 is a functional diagram illustrating a programmed computer system for performing imputation-based processing of genetic information in accordance with some embodiments. As will be apparent, other computer system architectures and configurations can be used to perform imputation-based processing of genetic information. Computer system 100, which includes various subsystems as described below, includes at least one microprocessor subsystem (also referred to as a processor or a central processing unit (CPU)) 102. For example, processor 102 can be implemented by a single-chip processor or by multiple processors. In some embodiments, processor 102 is a general purpose digital processor that controls the operation of the computer system 100. Using instructions retrieved from memory 110, the processor 102 controls the reception and manipulation of input data, and the output and display of data on output devices (e.g., display 118). In some embodiments, processor 102 includes and/or is used to perform imputation as described below.

Processor 102 is coupled bi-directionally with memory 110, which can include a first primary storage, typically a random access memory (RAM), and a second primary storage area, typically a read-only memory (ROM). As is well known in the art, primary storage can be used as a general storage area and as scratch-pad memory, and can also be used to store input data and processed data. Primary storage can also store programming instructions and data, in the form of data objects and text objects, in addition to other data and instructions for processes operating on processor 102. Also as is well known in the art, primary storage typically includes basic operating instructions, program code, data, and objects used by the processor 102 to perform its functions (e.g., programmed instructions). For example, memory 110 can include any suitable computer-readable storage media, described below, depending on whether, for example, data access needs to be bi-directional or uni-directional. For example, processor 102 can also directly and very rapidly retrieve and store frequently needed data in a cache memory (not shown).

A removable mass storage device 112 provides additional data storage capacity for the computer system 100, and is coupled either bi-directionally (read/write) or uni-directionally (read only) to processor 102. For example, storage 112 can also include computer-readable media such as magnetic tape, flash memory, PC-CARDS, portable mass storage devices, holographic storage devices, and other storage devices. A fixed mass storage 120 can also, for example, provide additional data storage capacity. The most common example of mass storage 120 is a hard disk drive. Mass storage 112, 120 generally store additional programming instructions, data, and the like that typically are not in active use by the processor 102. It will be appreciated that the information retained within mass storage 112 and 120 can be incorporated, if needed, in standard fashion as part of memory 110 (e.g., RAM) as virtual memory.

In addition to providing processor 102 access to storage subsystems, bus 114 can also be used to provide access to other subsystems and devices. As shown, these can include a display monitor 118, a network interface 116, a keyboard 104, and a pointing device 106, as well as an auxiliary input/output device interface, a sound card, speakers, and other subsystems as needed. For example, the pointing device 106 can be a mouse, stylus, track ball, or tablet, and is useful for interacting with a graphical user interface.

The network interface 116 allows processor 102 to be coupled to another computer, computer network, or telecommunications network using a network connection as shown. For example, through the network interface 116, the processor 102 can receive information (e.g., data objects or program instructions) from another network or output information to another network in the course of performing method/process steps. Information, often represented as a sequence of instructions to be executed on a processor, can be received from and outputted to another network. An interface card or similar device and appropriate software implemented by (e.g., executed/performed on) processor 102 can be used to connect the computer system 100 to an external network and transfer data according to standard protocols. For example, various process embodiments disclosed herein can be executed on processor 102, or can be performed across a network such as the Internet, intranet networks, or local area networks, in conjunction with a remote processor that shares a portion of the processing. Additional mass storage devices (not shown) can also be connected to processor 102 through network interface 116.

An auxiliary I/O device interface (not shown) can be used in conjunction with computer system 100. The auxiliary I/O device interface can include general and customized interfaces that allow the processor 102 to send and, more typically, receive data from other devices such as microphones, touch-sensitive displays, transducer card readers, tape readers, voice or handwriting recognizers, biometrics readers, cameras, portable mass storage devices, and other computers.

In addition, various embodiments disclosed herein further relate to computer storage products with a computer readable medium that includes program code for performing various computer-implemented operations. The computer-readable medium is any data storage device that can store data which can thereafter be read by a computer system. Examples of computer-readable media include, but are not limited to, all the media mentioned above: magnetic media such as hard disks, floppy disks, and magnetic tape; optical media such as CD-ROM disks; magneto-optical media such as optical disks; and specially configured hardware devices such as application-specific integrated circuits (ASICs), programmable logic devices (PLDs), and ROM and RAM devices. Examples of program code include both machine code, as produced, for example, by a compiler, or files containing higher level code (e.g., script) that can be executed using an interpreter.

The computer system shown in FIG. 1 is but an example of a computer system suitable for use with the various embodiments disclosed herein. Other computer systems suitable for such use can include additional or fewer subsystems. In addition, bus 114 is illustrative of any interconnection scheme serving to link the subsystems. Other computer architectures having different configurations of subsystems can also be utilized.

Figure 2:
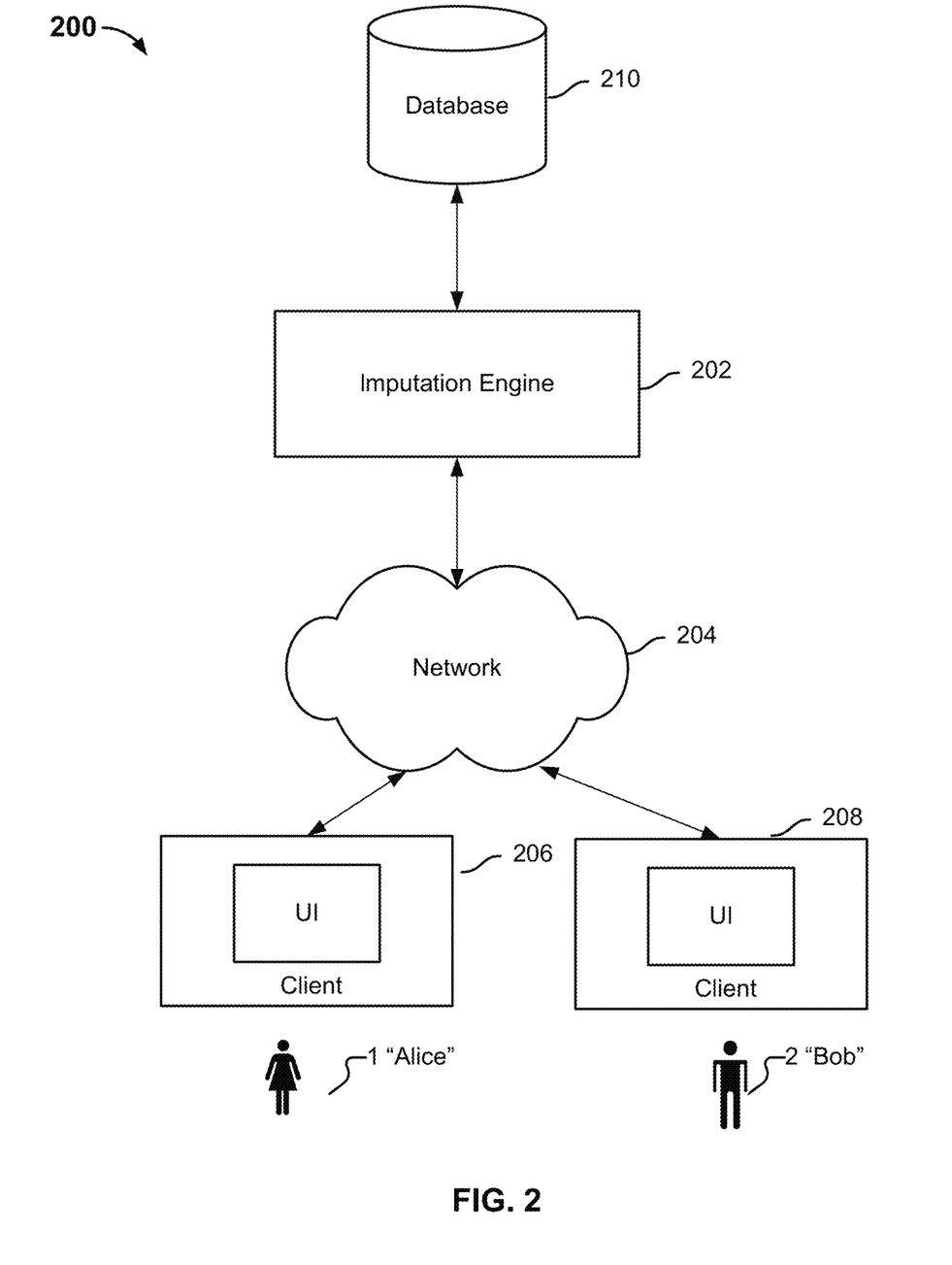
FIG. 2 is a block diagram illustrating an embodiment of a platform configured to process genetic information based on imputation.

FIG. 2 is a block diagram illustrating an embodiment of a platform configured to process genetic information based on imputation. In this example, imputation-based genetic information processing system 202 (also referred to as the imputation engine) may be implemented using one or more computers having one or more processors, one or more special purpose computing appliances, or any other appropriate hardware, software, or combinations thereof. The operations of the imputation engine are described in greater detail below.

In this example, personal information (including a combination of genetic information, phenotype information, family information, and/or population group information) pertaining to a plurality of candidate individuals is stored in a database 210, which can be implemented on an integral storage component of the imputation engine, an attached storage device, a separate storage device accessible by the imputation engine, or a combination thereof.

At least a portion of the database includes genotype data, specifically genotype data of genetic markers of individuals' deoxyribonucleic acid (DNA). Examples of such genetic markers include Single Nucleotide Polymorphisms (SNPs), which are points along the genome each corresponding to two or more common variations; Short Tandem Repeats (STRs), which are repeated patterns of two or more repeated nucleotide sequences adjacent to each other; and Copy-Number Variants (CNVs), which include longer sequences of DNA that could be present in varying numbers in different individuals. Although SNP-based genotype data is described extensively below for purposes of illustration, the technique is also applicable to other forms of genotype data such as STRs, CNVs, etc.

In this example, genotype data is used to represent the individuals' genomes instead of full sequence data. In some embodiments, the genotype data is obtained from DNA samples such as saliva or blood submitted by individuals. The laboratory analyzes the samples using a genotyping platform, for example the Illumina OmniExpress™ genotyping chip, which includes probes to assay allele values for a specific set of SNPs. One genotyping process is known as hybridization and yields different hybridization intensity values for each allele. The laboratory assigns genotype values to the alleles of each SNP by comparing the relative strength of these intensities. The resulting genotype data is stored in database 210 as a first set of genotype data. Other genotyping techniques can be used.

In some embodiments, this first set of genotype data is referred to as sparsely assayed data. A second set of reference genotype data (referred to as densely assayed data) is optionally stored. The reference genotype data includes more densely assayed genotype data and can be full genome sequence data. Compared with sparsely assayed data, densely assayed data includes greater amounts of genotype information as more locations on the chromosomes are assayed. In some embodiments, densely assayed data is obtained by combining results from multiple chips each assaying a different set of markers. For example, one chip assays chromosome locations 1 and 10, another chip assays chromosome locations 3 and 13, and the results are combined to produce densely assayed data at chromosome locations 1, 3, 10, and 13. In some embodiments, densely assayed data is obtained using genotyping platforms that assay a greater density of genetic markers (e.g., Illumina Omni2.5™ or Omni5™) or sequence the full genome (e.g., ABI SOLiD™.) In some embodiments, a combination of the techniques is used to obtain the reference data.

Information pertaining to one or more VOIs, and optionally additional information such as genotype information of a proband (i.e., an individual who has the VOI), is input into the imputation engine. The imputation engine identifies one or more matching individuals deemed likely to have the VOI even though the genotype information corresponding to the location of the VOI is not directly assayed. Examples of imputation technique include building a statistical model to perform statistical imputation, identifying Identical by Descent (IBD) regions, or a combination thereof.

In some embodiments, the imputation engine is a part of a personal genomic services platform providing a variety of services such as genetic counseling, ancestry finding, social networking, etc. In some embodiments, individuals whose data is stored in database 210 are registered users of a personal genomic service platform, which provides access to the data and a variety of personal genetics related services that the individuals have consented to participate in. Users such as Alice and Bob are genotyped and their genotype data is stored in database 210. They access the platform via a network 204 using client devices such as 206 and 208, and interacts with the platform via appropriate user interfaces (UIs) and applications. A variety of additional actions are possible. For example, in various embodiments, the correlation of having the VOI and having a certain phenotype such as a particular disease is determined; the matching individuals are recruited for further studies, notified of potential disease risk due to high correlation of having the genotype and having the disease, offered tips of possible preventive measures, etc.

Figure 3:
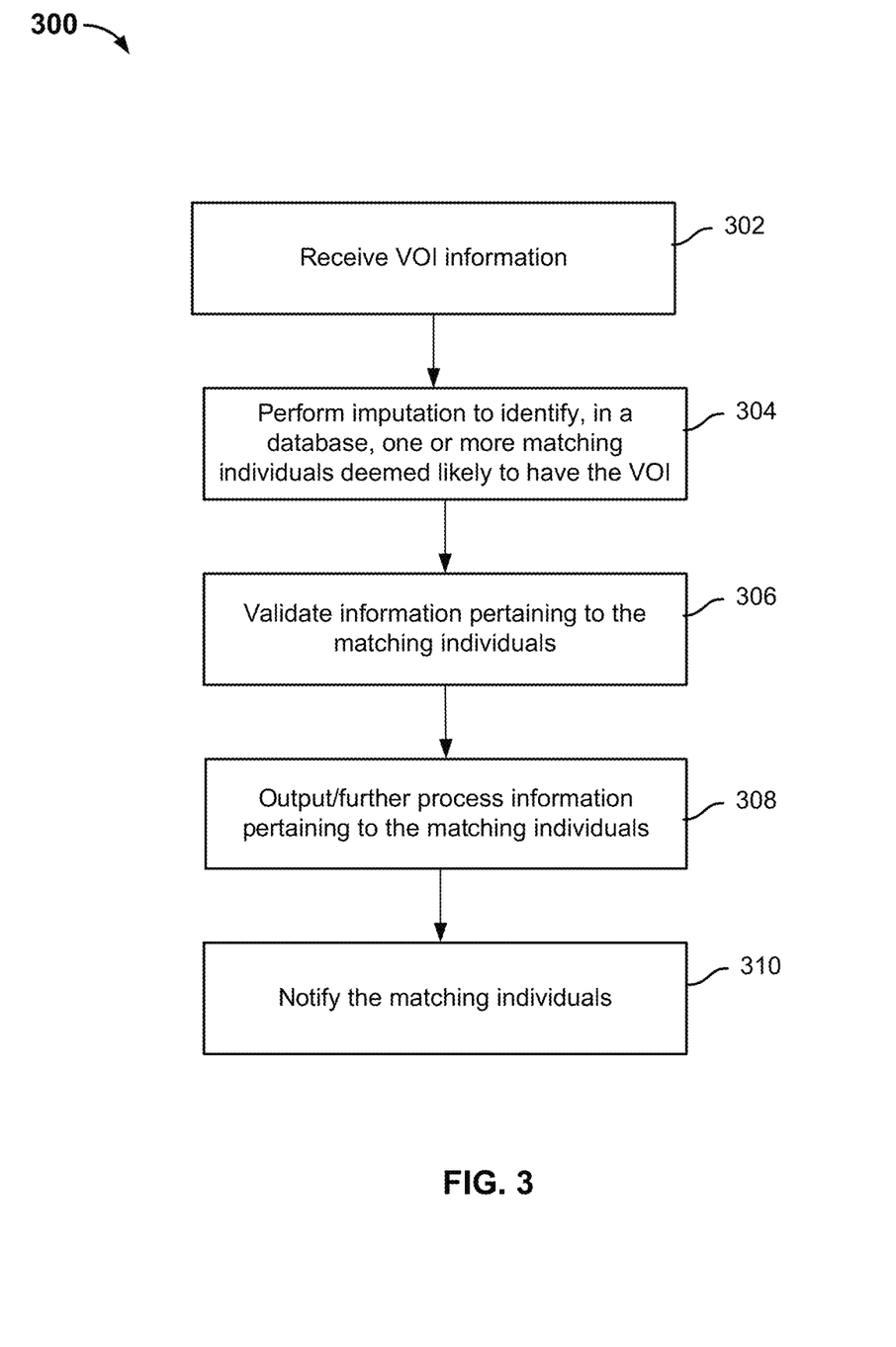
FIG. 3 is a flowchart illustrating an embodiment of a genetic information analysis process.

FIG. 3 is a flowchart illustrating an embodiment of a genetic information analysis process. In some embodiments, process 300 is performed on a system such as 100 or 202.

At 302, an input that includes information pertaining to a specific genetic variant (also referred to as the VOI) is received. For example, the input indicates that the VOI corresponds to G/C alleles at location 150 on Chromosome 3. Depending on the application, the significance of the VOI can be unknown or known. For example, in associative studies, the significance of the VOI is unknown since the purpose of the study is to determine whether certain phenotypes are associated (e.g., correlated) with the VOI. Thus, when a cohort of matching individuals is formed, their phenotype information is further processed to determine whether there are any associations of phenotypes with the VOI. In genetic counseling or risk analysis applications, the VOI is known to be associated with certain phenotype expressions and matching individuals identified as having the VOI are warned of the potential risk for developing a disease, notified of the known association, provided with disease prevention tips and other related information. In some embodiments, the input further includes additional genotype information of a proband whose genome includes the VOI. The additional genotype information can include a set of genetic markers or a full genome sequence.

At 304, imputation is performed to identify, in a database, one or more matching individuals deemed likely to have the specific genetic variant. The set of matching individuals is referred to as a cohort. As discussed above in connection with FIG. 2, the database comprises genotype information of a plurality of candidate individuals, and genotype information of the matching individual pertaining to the specific genetic variant (e.g., genotype information at the variant location) is not directly assayed. As will be described in greater detail below, techniques such as statistical imputation, IBD region identification, and the like are used to determine which individuals are likely to have the VOI.

Optionally, at 306, validation is performed to ensure that the variant is not a private mutation (a mutation present in one person or family), or a de novo mutation (specifically, a new mutation in an individual). In some embodiments, once the cohort is formed, the genetic information of one or more matching individuals in the cohort is assayed directly to verify whether the mutation is not private or de novo. In other words, DNAs of one or more individuals from the cohort are directly assayed (e.g., sequenced or using chips with a specific probe at the VOI location) to determine whether they actually possess the VOI. If the direct assay results confirm that the individuals have the VOI, then the VOI is not a private or de novo mutation; otherwise the VOI is likely a private or de novo mutation rather than a VOI shared by the cohort.

Optionally, at 308, cohort data is output and/or further processed. For example, statistical analysis such as phenotypic association of the VOI is performed in some embodiments to determine whether having the VOI is correlated with having certain phenotype such as a particular disease or condition.

Optionally, at 310, matching individuals in the cohort are notified, preferably via a personal genomic services platform such as 200. Depending on system configuration, the individuals may be notified via email, text messages, system messages, or any other appropriate communication channel. Depending on the application, the individuals may receive different types of notification. In embodiments where the cohort is identified for associative studies of a VOI of unknown significance, the individuals in the cohort are invited to participate in these studies; in embodiments where users have previously indicated interest in receiving genetic counseling/risk analysis information and the VOI is known to be correlated with certain phenotype, the individuals in the cohort are notified of the correlation and provided with information such as the specific risk, prevention tips, etc.

Statistical Imputation

In some embodiments, imputation includes statistical imputation. A statistical model such as a haplotype graph is established based on a set of reference individuals with densely assayed data. Sparsely assayed genotype data of a candidate individual (i.e., an individual whose genotype corresponding to the VOI location is not directly assayed) is applied to the statistical model to impute whether that individual possesses the VOI.

The standard SNP-based genotyping technology results in genotype calls each having two alleles, one from each half of a chromosome pair. As used herein, a genotype call refers to the identification of the pair of alleles at a particular locus on the chromosome. Genotype calls can be phased or unphased. In phased data, the individual's diploid genotype at a particular locus is resolved into two haplotypes, one for each chromosome. In unphased data, the two alleles are unresolved; in other words, it is uncertain which allele corresponds to which haplotype or chromosome. Phasing can be done using known phasing tools such as BEAGLE. Either phased data or unphased data can be used in the imputation process; for purposes of illustration examples using phased data are discussed with respect to the statistical imputation process.

Examples of sparsely assayed data of candidate individuals and densely assayed data of reference individuals are illustrated in Tables 1 and 2, respectively.

TABLE 1

| | Genotype Data | | | | | Phenotype Data | |
|---|---|---|---|---|---|---|---|
| ID | 100 | 200 | 300 | 400 | ... | Disease X? | Disease Y? ... |
| U1 | G | T | A | C | ... | Yes | No |
| U2 | A | C | G | G | | No | No |
| U3 | G | A | C | A | | No | Unknown |
| ... | ... | ... | ... | ... | ... | ... | ... |

Table 1 illustrates an example data set of sparsely assayed genotype data and phenotype data of candidate individuals. In some embodiments, the data is obtained using assaying chips or other genotyping hardware, and is stored in a database such as 210. In this example, data for an individual is stored in a row. The genotype data of each individual comprises a set of SNPs with values such as A, C, G, or T at specific locations on a chromosome. For purposes of simplicity, this example assumes that phased data is used, and unphased data can be processed using known phasing techniques such as BEAGLE to obtain phased data. For purposes of illustration, the genotype data includes N SNPs, shown to be assayed at every $100^{th}$ location on the chromosome (i.e., at locations 100, 200, 300, and 400); other locations may be used in other implementations. This set of genotype data is sparsely assayed data. Phenotype data such as whether the individual has a particular disease or condition is also stored. Other data formats may be used in other embodiments.

To perform statistical imputation, a reference data set of densely assayed data is used to construct a statistical model (e.g., a haplotype graph) used to determine likely genotype sequences for the candidate individuals. Table 2 illustrates an example data set of reference data. For purposes of illustration, the reference data includes L SNPs, assayed at every $20^{th}$ location at locations 20, 40, 60, 80, 100, etc. Other locations may be used in other embodiments. In some embodiments, full genome sequences are used. The number of reference individuals in the densely assayed reference data set is typically fewer than the number of candidate individuals in the sparsely assayed data set. For example, there can be 100,000 or more individuals in the sparsely assayed data set, but only 1000 in the densely assayed data set.

TABLE 2

| | Genotype Data | | | | | | | | |
|---|---|---|---|---|---|---|---|---|---|
| ID | 20 | 40 | 60 | 80 | 100 | 120 | 140 | 160 | ... |
| R1 | A | A | G | A | C | T | T | G | ... |
| R2 | A | G | T | C | C | T | A | G | ... |
| R3 | G | T | A | A | T | C | G | C | ... |
| ... | ... | ... | ... | ... | ... | ... | ... | ... | ... |

Figure 4:
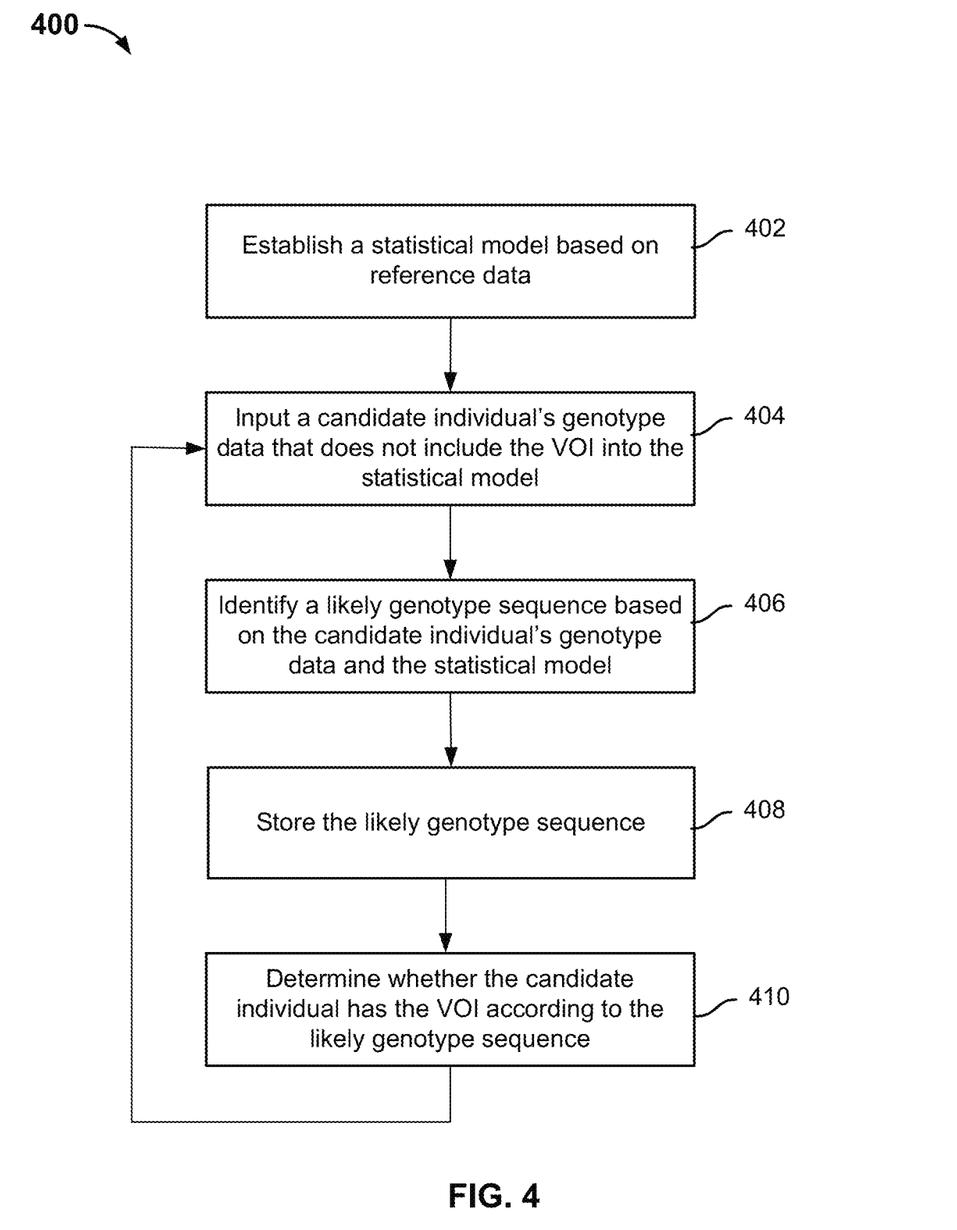
FIG. 4 is a flowchart illustrating an embodiment of a statistical imputation process.

FIG. 4 is a flowchart illustrating an embodiment of a statistical imputation process. In some embodiments, process 400 is used to implement step 304 of process 300.

At 402, a statistical model is established based on the reference data comprising densely assayed genotype data. In some embodiments, the statistical model includes a haplotype graph that represents the genotype data of the reference population. The reference data includes genotype information corresponding to the VOI location.

Figure 5:
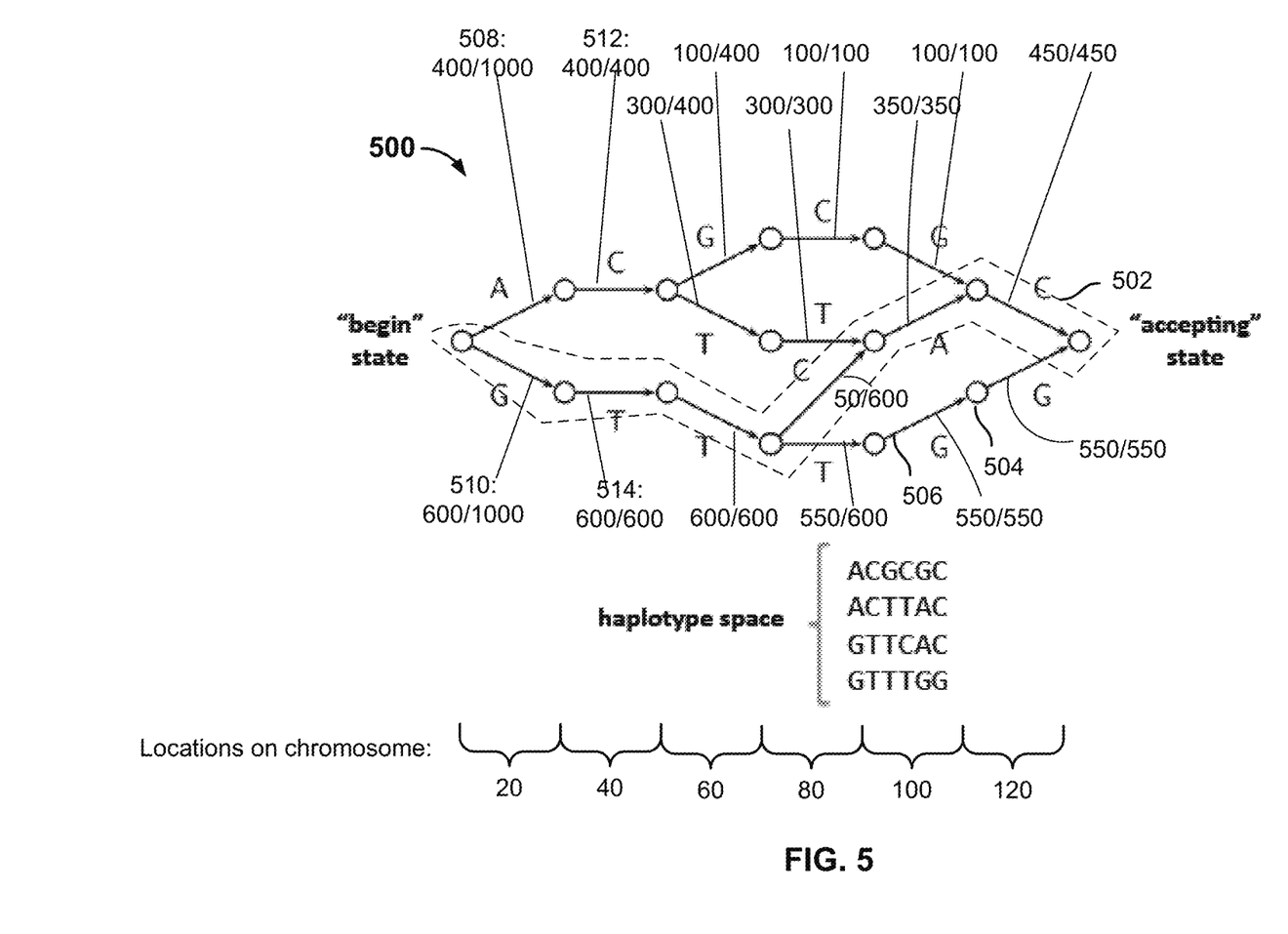
FIG. 5 is a diagram illustrating an example of a haplotype graph that is constructed based on a reference collection of genotype data.

FIG. 5 is a diagram illustrating an example of a haplotype graph that is constructed based on a reference collection of genotype data. In this example, the reference collection of genotype data includes a set of L (L=6 in this case) genetic markers (e.g., SNPs) measured at locations 20, 40, 60, 80, 100, and 120 on a particular chromosome. In other embodiments, different L and different locations can be used. The reference data includes directly assayed genotype information corresponding to the VOI location. For example, if the VOI is located at location 80 of the chromosome, the genotype of the reference individuals' genome at this location is directly assayed and the information is included in the reference genotype data.

As shown, haplotype graph 500 is a Directed Acyclic Graph (DAG) having nodes (e.g., 504) and edges (e.g., 506). To construct a haplotype graph, each reference individual's genotype data forms a path. Identical portions of the paths are combined to form nodes and edges of the graph. The haplotype graph starts with a single node (the "begin state")

and ends on a single node (the "accepting state"), and the intermediate nodes correspond to the states of the markers at respective gene loci. There are a total of L+1 levels of nodes from left to right. An edge, e, represents the set of haplotypes whose path from the initial node to the terminating node of the graph traverses e. The possible paths define the haplotype space of possible genotype sequences. For example, in haplotype graph 500, a path 502 corresponds to the genotype sequence "GTTCAC." In the example shown, there are four possible paths/genotype sequences in the haplotype space shown in this diagram ("ACGCGC," "ACTTAC," "GTTCAC," and "GTTTGG"). Given a greater number of reference individuals and longer genotype sequences, the resulting haplotype graph would be a more complex structure having a greater number of nodes and possible paths.

Each edge in the haplotype graph is associated with a probability computed based on the reference collection of densely assayed genotype data. In this example, the reference collection is comprised of genotype data from 1000 individuals, of which 400 have the "A" allele at the first position (in this case, location 20 on the chromosome), and 600 have the "G" allele at the first position. Accordingly, the probability associated with edge 508 is 400/1000 and the probability associated with edge 510 is 600/1000. All of the first 400 individuals have the "C" allele at the second position (location 40 on the chromosome), giving edge 512 a probability of 400/400. All of the next 600 individuals who had the "G" allele at the first position have the "T" allele at the second position, giving edge 514 a probability of 600/600, and so on. The probabilities associated with the respective edges are labeled in the diagram. The probability associated with a specific path is expressed as the product of the probabilities associated with the edges included in the path. For example, the probability associated with path 502 ("GTTCAC") is computed as:

$$P(h) = \left(\frac{600}{1000}\right)\left(\frac{600}{600}\right)\left(\frac{600}{600}\right)\left(\frac{50}{600}\right)\left(\frac{350}{350}\right)\left(\frac{450}{450}\right) = 0.05$$

Returning to FIG. 4, at 404, genotype data of a candidate individual whose genotype at the position corresponding to the VOI is not directly assayed is input into the statistical model. In some embodiments, sparsely genotyped data of the candidate individual is applied as inputs to the haplotype graph.

At 406, a likely genotype sequence is identified based on the candidate individual's genotype data and the statistical model. In some embodiments, at least a portion of the sparsely genotyped data (e.g., a portion that overlaps the VOI location) is compared with paths on the haplotype graph to find a most likely path (i.e., a likely genotype sequence). Referring again to FIG. 5 for an example: suppose that the only assayed SNP in the individual's genome corresponds to the SNP at the fifth position of the haplotype graph (location 100 on the chromosome) and is "A." Accordingly, there are two possible paths identified for this individual: "GTTCAC" (path 502) and "ACTTAC." The probability associated with the path "ACTTAC" is computed as:

$$P(h) = \left(\frac{400}{1000}\right)\left(\frac{400}{400}\right)\left(\frac{300}{400}\right)\left(\frac{300}{300}\right)\left(\frac{350}{350}\right)\left(\frac{450}{450}\right) = 0.3$$

Further, as discussed above, the probability associated with path "GTTCAC" is 0.05. Thus, it is more likely that the individual's genotype sequence follows the "ACTTAC" path instead of the "GTTCAC" path. In other words, the individual is imputed to have A, C, T, T, and C at locations 20, 40, 60, 80, and 120 of the chromosome even though only the SNP at location 100 is directly assayed.

In some embodiments, to determine the most likely path, all possible paths are identified based on the assayed SNPs and the probability associated with each possible path is determined to find the most likely one. In some embodiments, instead of computing all possible paths, a dynamic programming technique is used to improve computational efficiency. In some embodiments, instead of the most likely full path, a most likely portion of a path (e.g., a portion of a genotype sequence that overlaps the VOI location) is determined. In some embodiments, the portion size is empirically determined and depends on the length of the haplotypes, which can vary depending on the amount of recombination in a region and the relative age of the variant.

At 408, the likely genotype sequence is optionally stored to facilitate VOI lookups. Future VOI determinations will not require the sequence to be recomputed; instead, the stored likely genotype sequence is looked up, and performance is improved.

At 410, whether the candidate individual has the VOI is determined according to the likely genotype sequence. Referring again to FIG. 5, suppose that the VOI is "C" at location 80 of the chromosome (the fourth position on the haplotype graph). In the event that the most likely path of a candidate individual is "ACTTAC," the variant at location 80 (the fourth position of the sequence) is imputed to be "T" and the individual is imputed not to have the VOI. In the event that the most likely path of the individual follows "GTTCAC" (possibly determined as a result of other matches to locations not shown on the haplotype graph of FIG. 5, such as locations 200, 300, etc.), the variant at location 80 is imputed to be "C" and the individual is imputed to have the VOI.

In some embodiments, 402-410 are repeated (e.g., executed multiple times sequentially or in parallel) for a plurality of individuals whose genome is sparsely assayed. Individuals deemed to likely have the VOI form a cohort.

As discussed above, the reference individuals' genotype information is more densely assayed than that of the candidate individuals. In some embodiments, the haplotype graph is used to help determine locations in the candidate individuals' genome to assay. For example, referring to FIG. 5, locations where the haplotype graph branches out (e.g., location 20 with the A/G branch, location 60 with the G/T branch, location 80 with the C/T branch) have more information and would improve the accuracy of identification of the likely paths of the candidate individuals. Thus, if the candidate individuals have not been assayed already or if re-assaying is permitted, the system can opt to assay the candidate individuals at locations 20, 60, and/or 80 instead of 100.

Identity by Descent (IBD)-Based Imputation

In some embodiments, imputation includes identifying IBD regions between a proband and a candidate individual. IBD-based imputation does not require a reference set of densely assayed genotype data.

Because of recombination and independent assortment of chromosomes, the autosomal DNA and X chromosome DNA (collectively referred to as recombining DNA) from the parents are shuffled at the next generation, with small amounts of mutation. Relatives (i.e., people who descended from the same ancestor) will share long stretches of genome regions where their recombining DNA is completely or nearly identical. Such regions are referred to as "Identity (or Identical) by Descent" (IBD) regions because they arose from the same DNA sequences in an earlier generation. In some embodiments, individuals in the database that share a variant-overlapping IBD region with the proband are identified. A variant-overlapping IBD region is an IBD region that overlaps the location where the VOI is found.

In some embodiments, the determination of IBD regions includes comparing the DNA markers (e.g., SNPs, STRs, CNVs, etc.) of two individuals. The standard SNP based genotyping technology results in genotype calls each having two alleles, one from each half of a chromosome pair. As used herein, a genotype call refers to the identification of the pair of alleles at a particular locus on the chromosome.

Figure 6:
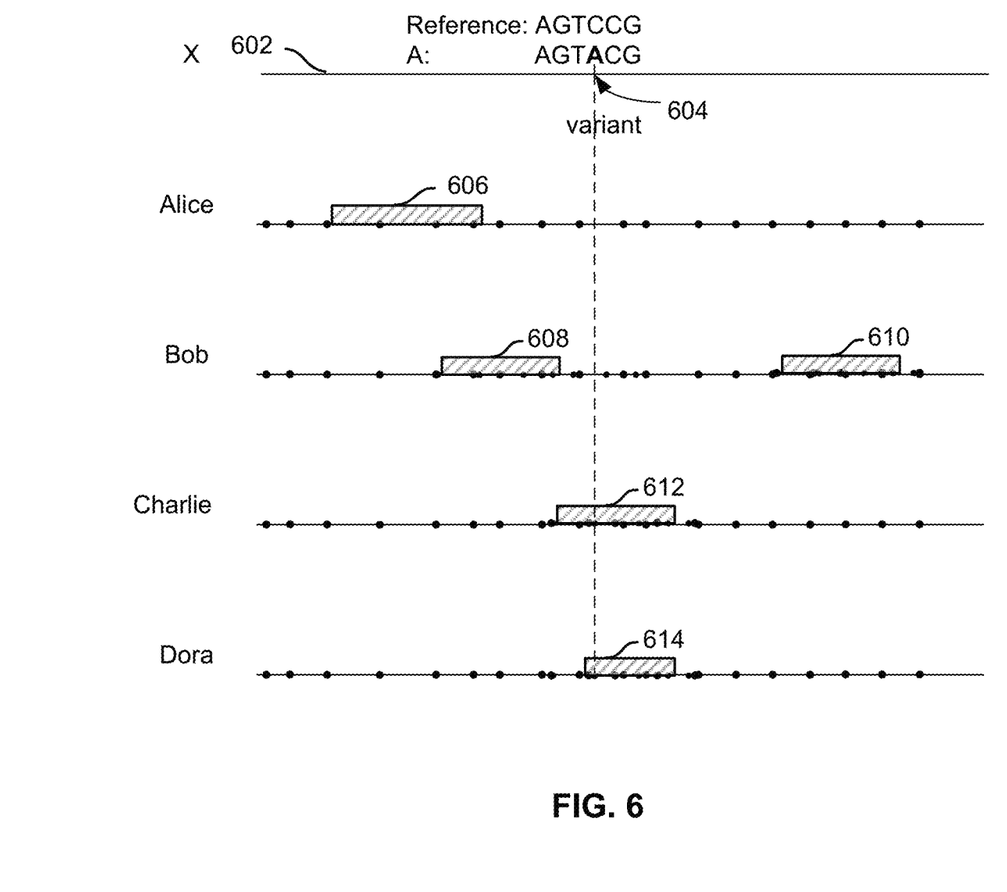
FIG. 6 is a diagram illustrating an example of VOI identification based on IBD.

FIG. 6 is a diagram illustrating an example of VOI identification based on IBD. In this example, the phase haplotype of the proband, X, is represented by line 602. A particular VOI in X's genome is identified at location 604. The sequence of a reference genotype overlapping this location is "AGTCCG," and the sequence of X's genome is "AGTACG" (the second A being the VOI). X's genome can be fully sequenced, or genotyped and in addition have the variant at 604 specifically identified. Note that the technique of identifying the variant at 604 need not be the same as assaying the SNP variant used to compute IBD between X and other individuals in the database.

In this example, Alice, Bob, Charlie, and Dora are candidate individuals whose genotype information is stored in the database. The number of candidate individuals in the database can be much greater in practice. Note that the genotype information of these candidate individuals at location 604 is not directly assayed. The chips used to assay their DNA samples in this case produce SNPs at other locations of the individuals' genome. The SNPs are represented as dots on the line.

It is determined whether individuals in the database (such as Alice, Bob, Charlie, and Dora) have DNA segments overlapping the variant location 604 that is IBD with respect to X's genome. IBD identification can be performed using existing IBD identification techniques such as fastIBD. In this case, although Alice shares an IBD region 606 (shown as the shaded box) with X, region 606 does not overlap the variant location; Bob shares IBD regions 608 and 610 with X, but neither region overlaps the variant location; Charlie shares IBD region 612 with X, and this region overlaps the variant location; Dora shares IBD region 614 with X, and this region also overlaps the variant location. These IBD segments are typically short (e.g., <10 centimorgans (cM)) and often belong to distant relatives who share only one segment with the proband. Since the IBD regions are supposed to be identical between individuals, although the sequence information for location 604 is not necessarily known for individuals Charlie and Dora, because they share IBD regions with X that overlap the variant location, it is imputed that Charlie and Dora would also have the same variant at location 604 (in this case, "AGTACG"). In this case, Charlie and Dora are deemed to be matching individuals since they both share variant-overlapping IBD regions with X (and therefore are assumed to have the same VOI).

In some embodiments, the genotype and/or phenotype information of Charlie and Dora is output and can be used for a variety of purposes. For example, Charlie and Dora can be included in a cohort for statistical analysis, testing for phenotypic association with this particular variant, etc. For instance, the technique can be used to test rare mutations (particularly ones that are not present on the genotyping chip and therefore not genotyped) in cancer genes to determine (or validate existing theories on) whether specific mutations are associated with increased odds of getting a particular type of cancer or are benign polymorphisms that are not associated with increased risk of getting that type of cancer.

In some embodiments, further validation is performed to confirm that the variant is not a private mutation or a de novo mutation. Using the example above, once it is established that Charlie and Dora are in the cohort, if further assaying of Charlie and Dora's genetic materials shows that neither has the same variant as X at location 604, then it is likely that X's variant is private or de novo. If, however, Charlie and/or Dora have the same variant, then it is unlikely that X's variant is private or de novo.

Figure 7:
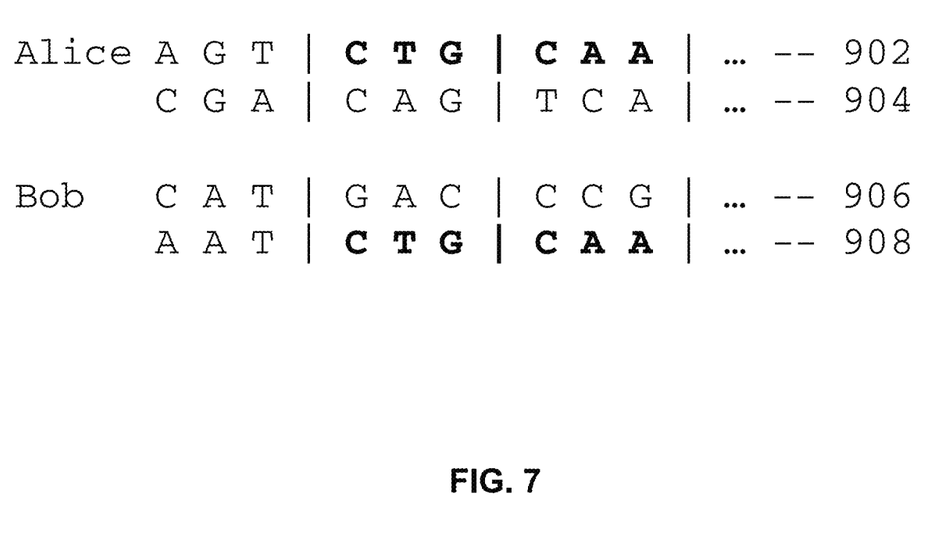
FIG. 7 is a diagram illustrating an example in which phased data is compared to identify IBD.

In some embodiments, sequences of SNPs are stored in dictionaries using a hash-table data structure for the ease of comparison. FIG. 7 is a diagram illustrating an example in which phased data is compared to identify IBD. The sequences are split along pre-defined intervals into non-overlapping words. Other embodiments may use overlapping words. Although a preset length of 3 is used for purposes of illustration in the example shown, many implementations may use words of longer lengths (e.g., 100). Also, the length does not have to be the same for every location. In FIG. 7, on Alice's chromosome pair 1, phased haplotype 902 is represented by words AGT, CTG, CAA, . . . and phased haplotype 904 is represented by CGA, CAG, TCA, . . . . At each location, the words are stored in a hash table that includes information about a plurality of individuals to enable constant retrieval of which individuals carry matching haplotypes. Similar hash tables are constructed for other sequences starting at other locations. To determine whether Bob's chromosome pair 1 shares any IBD with Alice's, Bob's sequences are processed into words at the same locations as Alice's. Thus, Bob's haplotype 906 yields CAT, GAC, CCG, . . . and haplotype 908 yields AAT, CTG, CAA, . . . . Every word from Bob's chromosomes is then looked up in the corresponding hash table to check whether any other users have the same word at that location in their genomes. In the example shown, the second and third words of haplotype 908 match second and third words of Alice's haplotype 902. This indicates that SNP sequence CTGCAA is present in both chromosomes and suggests the possibility of IBD sharing. If enough matching words are present in close proximity to each other, the region would be deemed IBD.

Figure 8:
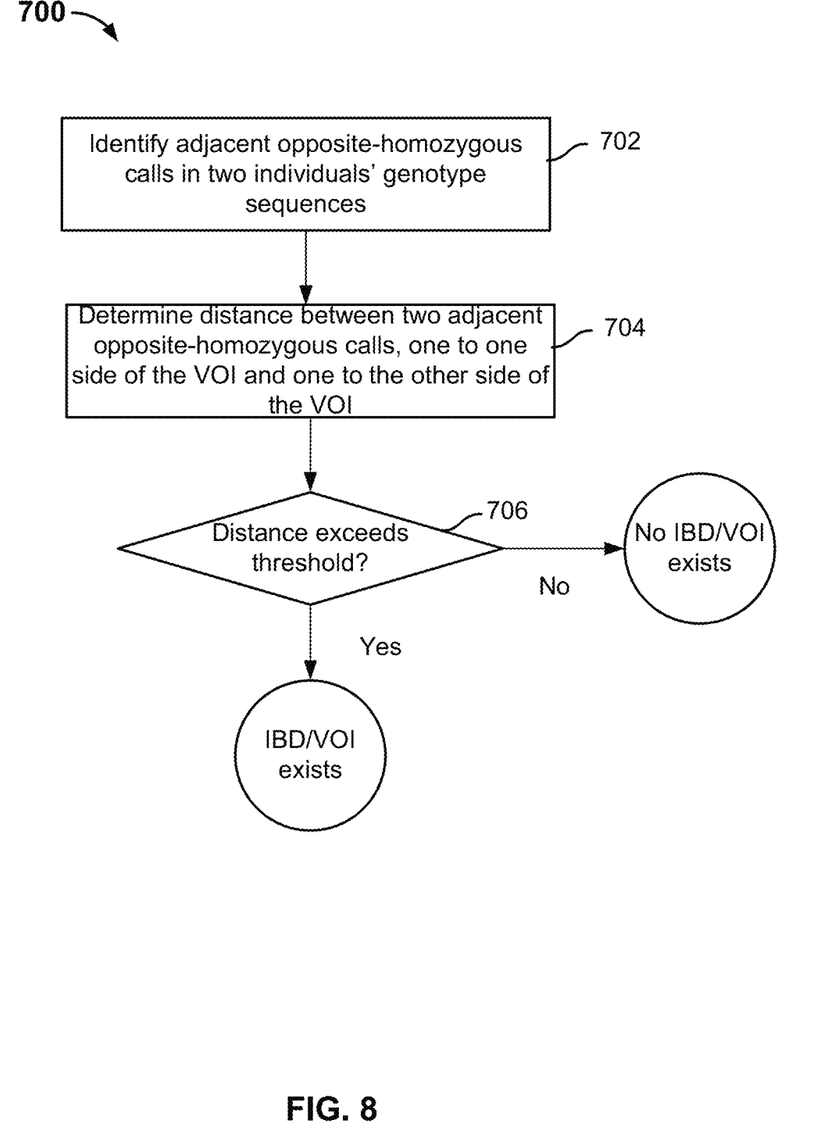
FIG. 8 is a diagram illustrating an embodiment of another IBD-based imputation process.

FIG. 8 is a diagram illustrating an embodiment of another IBD-based imputation process. Process 700 may be used to implement 304 of process 300 and is applicable to unphased data.

The genotype call at a particular SNP location may be a heterozygous call with two different alleles or a homozygous call with two identical alleles. A heterozygous call is represented using two different letters such as AB that correspond to different alleles. Some SNPs are biallelic SNPs with only two possible states for SNPs. Some SNPs have more states, e.g., triallelic. Other representations are possible.

In this example, the letter "A" is selected to represent an allele with base A and the letter "B" represents an allele with base G at the SNP location. Other representations are possible. A homozygous call is represented using a pair of identical letters such as AA or BB. The two alleles in a homozygous call are interchangeable because the same allele came from each parent. When two individuals have opposite-homozygous calls at a given SNP location, or, in other words, one person has alleles AA and the other person has alleles BB, it is very likely that the region in which the SNP resides does not have IBD since different alleles came from different ancestors. If, however, the two individuals have compatible calls, that is, both have the same homozygotes (i.e., both people have AA alleles or both have BB alleles), both have heterozygotes (i.e., both people have AB alleles), or one has a heterozygote and the other a homozygote (i.e., one has AB and the other has AA or BB), there is some chance that at least one allele is passed down from the same ancestor and therefore the region in which the SNP resides is IBD. Further, based on statistical computations, if a region has a very low rate of opposite-homozygote occurrence over a substantial distance, it is likely that the individuals inherited the DNA sequence in the region from the same ancestor and the region is therefore deemed to be an IBD region.

At 702, consecutive opposite-homozygous calls in two individuals' SNPs (e.g., the SNPs of the proband and the SNPs of a candidate individual) are identified. The consecutive opposite-homozygous calls can be identified by serially comparing individual SNPs in the individuals' SNP sequences or in parallel using bitwise operations. At 704, the distance between two adjacent opposite-homozygous calls located on either side of the VOI (e.g., one to the left side of the VOI and one to the right side of the VOI) is determined. The distance may be physical distance measured in the number of base pairs or genetic distance accounting for the rate of recombination. At 706, it is determined whether the distance between the opposite-homozygous calls exceeds a threshold. In some embodiments, the threshold value is set to 10 cM. If the threshold is exceeded, the region between the calls is determined to be an IBD region and VOI is imputed to exist in the candidate individual's genome.

In some embodiments, a tolerance for genotyping error can be built by allowing some low rate of opposite homozygotes when calculating an IBD segment. In some embodiments, the total number of matching genotype calls is also taken into account when deciding whether the region is IBD. For example, a region is optionally further examined where the distance between consecutive opposite homozygous calls is just below the 10 cM threshold. If a large enough number of genotype calls within that interval match exactly, the interval is still deemed IBD and VOI is deemed to exist.

Figure 9:
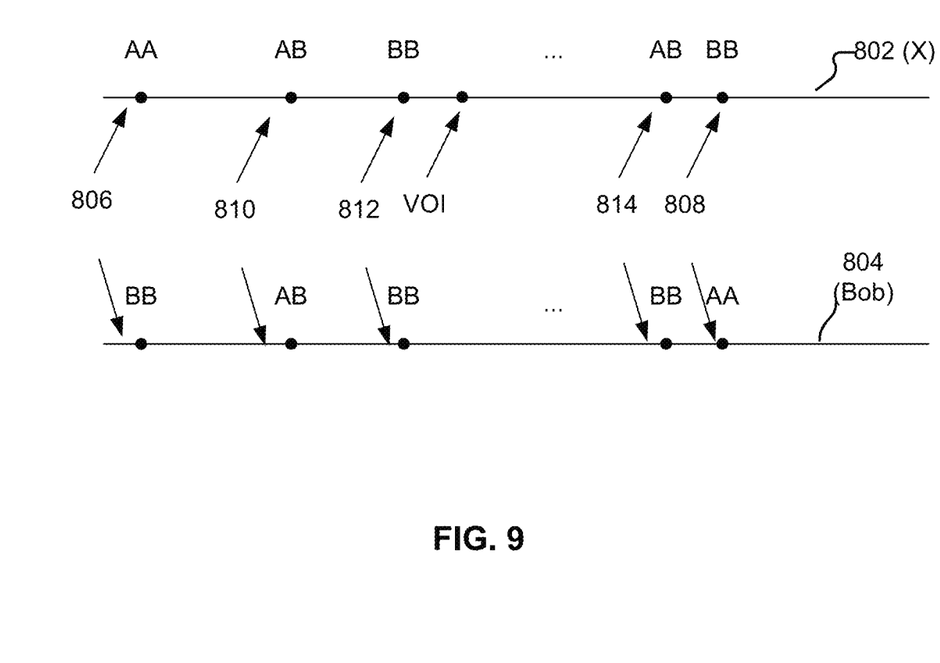
FIG. 9 is a diagram illustrating example genotype data used for IBD identification by process 700.

FIG. 9 is a diagram illustrating example genotype data used for IBD identification by process 700. 802 and 804 correspond to the SNP sequences of X and Bob, respectively. In this example, X is the proband and Bob is a candidate individual. At location 806, the alleles of X and Bob are opposite-homozygotes, suggesting that the SNP at this location resides in a non-IBD region. Similarly, at location 808, the opposite-homozygotes suggest a non-IBD region. At location 810, however, both pairs of alleles are heterozygotes, suggesting that there is potential for IBD. Similarly, there is potential for IBD at location 812, where both pairs of alleles are identical homozygotes, and at location 814, where X's pair of alleles is heterozygous and Bob's is homozygous. If there is no other opposite-homozygote between 806 and 808 and there are a large number of compatible calls between the two locations (e.g., the number of compatible calls meeting a predefined threshold), it is then likely that the region between 806 and 808 is an IBD region. Since the VOI is located between the adjacent opposite-homozygous pair 806 and 808, Bob is imputed to have the VOI due to sharing an IBD region with X.

In various embodiments, the effects of genotyping error are accounted for and corrected. In some embodiments, certain genotyped SNPs are removed from consideration if there are a large number of Mendelian errors when comparing data from known parent/offspring trios. In some embodiments, SNPs that have a high no-call rate or otherwise failed quality control measures during the assay process are removed. In some embodiments, in an IBD segment, an occasional opposite-homozygote is allowed if there is sufficient opposite-homozygotes-free distance (e.g., at least 3 cM and 300 SNPs) surrounding the opposite-homozygote.

In some embodiments, multiple imputation processes are pipelined to improve performance. For example, a statistical imputation process is performed first. If the process fails to find a match because, for example, the VOI does not exist in the haplotype graph, then an IBD-based imputation process is performed. Alternatively, IBD-based imputation can be performed first, and if no VOI is found, statistical imputation is performed next. In some embodiments, both statistical imputation and IBD-based imputation are performed regardless of success or failure of an individual process. Results from the processes (e.g., matching individuals A, B, and C found using a statistical imputation process and matching individuals A, D, and E found using an IBD-based process) are combined to form the cohort (e.g., A, B, C, D, and E).

Identifying in a database matching individuals who are imputed to have a specific genetic variant has been described. Imputation allows interested parties (e.g., researchers, service providers) to leverage genetic information in large databases to find matching individuals, even though the database does not necessarily have directly assayed information of the specific variant.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A genetic information processing system, comprising:
   computer memory storing one or more databases comprising densely sequenced genotype data of a plurality of reference individuals and sparsely sequenced genotype data and phenotype data of a plurality of candidate individuals; and
   one or more computer processors coupled to the computer memory, the one or more processors being configured to:
   (a) receive an input comprising information pertaining to a genetic variant of unknown significance (VUS);
   (b) retrieve the densely sequenced genotype data of the plurality of reference individuals from the one or more databases, wherein the densely sequenced genotype data comprises genotype data at a genetic locus corresponding to the VUS; and
   (c) perform statistical imputation, Identity by Descent (IBD)-based imputation, or a combination thereof on the sparsely sequenced genotype data of the plurality of candidate individuals using the densely sequenced genotype data of the plurality of reference individuals, thereby obtaining imputed genotype data with reference to the VUS for the plurality of candidate individuals, wherein the genetic locus corresponding to the VUS for the plurality of candidate individuals is not directly assayed by a genotyping chip or a genotyping platform.

2. The system of claim 1, wherein (c) comprises to perform statistical imputation.

3. The system of claim 1, wherein to perform statistical imputation comprises to:
   establish a statistical model based on genotype information of a set of reference individuals; and
   apply a candidate individual's genotype information to the statistical model to determine whether the candidate individual is a matching individual who has the VUS.

4. The system of claim 1, wherein (c) comprises to perform Identity by Descent (IBD)-based imputation.

5. The system of claim 4, wherein to perform IBD-based imputation includes to:
   receive additional genotype information of a proband who has the VUS; and
   determine whether a candidate individual shares a variant-overlapping IBD region with the proband.

6. The system of claim 5, wherein to determine whether the candidate individual shares a variant-overlapping IBD region with the proband includes to:
   determine a distance between two adjacent opposite-homozygous calls in the proband's genotype sequence and the candidate individual's genotype sequence, one of the two adjacent opposite-homozygous calls is to the left of the VUS and another one of the two adjacent opposite-homozygous calls is to the right of the VUS; and
   determine whether the distance meets a threshold.

7. The system of claim 3, wherein genetic material of the matching individual is further assayed to validate whether the matching individual actually possesses the VUS.

8. A method of processing genetic information, implemented using a computer system comprising one or more computer processors coupled to computer memory storing one or more databases comprising densely sequenced genotype data of a plurality of reference individuals and sparsely sequenced genotype data and phenotype data of a plurality of candidate individuals, the method comprising:
   (a) receiving, by the computer system, an input comprising information pertaining to a genetic variant of unknown significance (VUS);
   (b) retrieving, by the computer system, the densely sequenced genotype data of the plurality of reference individuals from the one or more databases, wherein the densely sequenced genotype data comprises genotype data at a genetic locus corresponding to the VUS; and
   (c) performing, by the one or more computer processors, statistical imputation, Identity by Descent (IBD)-based imputation, or a combination thereof on the sparsely sequenced genotype data of the plurality of candidate individuals using the densely sequenced genotype data of the plurality of reference individuals, thereby obtaining imputed genotype data with reference to the VUS for the plurality of candidate individuals, wherein the genetic locus corresponding to the VUS for the plurality of candidate individuals is not directly assayed by a genotyping chip or a genotyping platform.

9. The method of claim 8, wherein (c) comprises performing statistical imputation.

10. The method of claim 8, wherein performing statistical imputation comprises:
    establishing a statistical model based on genotype information of a set of reference individuals; and
    applying a candidate individual's genotype information to the statistical model to determine whether the candidate individual is a matching individual who has the VUS.

11. The method of claim 8, wherein (c) comprises performing IBD-based imputation.

12. The method of claim 11, wherein performing IBD-based imputation comprises:
    receiving additional genotype information of a proband who has the VUS; and
    determining whether a candidate individual shares a variant-overlapping IBD region with the proband.

13. The method of claim 12, wherein determining whether the candidate individual shares a variant-overlapping IBD region with the proband comprises:
    determining a distance between two adjacent opposite-homozygous calls in the proband's genotype sequence and the candidate individual's genotype sequence, one of the two adjacent opposite-homozygous calls is to the left of the VUS and another one of the two adjacent opposite-homozygous calls is to the right of the VUS; and
    determining whether the distance meets a threshold.

14. The method of claim 10, wherein genetic material of the matching individual is further assayed to validate whether the matching individual actually possesses the VUS.

15. A computer program product for processing genetic information using a computer system comprising one or more computer processors coupled to computer memory storing one or more databases comprising densely sequenced genotype data of a plurality of reference individuals and sparsely sequenced genotype data and phenotype data of a plurality of candidate individuals, the computer program product being embodied in a tangible computer readable storage medium and comprising computer instructions for:
    (a) receiving an input comprising information pertaining to a genetic variant of unknown significance (VUS);
    (b) retrieving the densely sequenced genotype data of the plurality of reference individuals from the one or more databases, wherein the densely sequenced genotype data comprises genotype data at a genetic locus corresponding to the VUS; and
    (c) performing statistical imputation, Identity by Descent (IBD)-based imputation, or a combination thereof on the sparsely sequenced genotype data of the plurality of candidate individuals using the densely sequenced genotype data of the plurality of reference individuals, thereby obtaining imputed genotype data with reference to the VUS for the plurality of candidate individuals, wherein the genetic locus corresponding to the VUS for the plurality of candidate individuals is not directly assayed by a genotyping chip or a genotyping platform.

16. A genetic information processing system, comprising:
    computer memory storing one or more databases comprising reference genotype data of a plurality of reference individuals and sparsely sequenced genotype data and phenotype data of a plurality of candidate individuals; and
    one or more computer processors coupled to the computer memory, the one or more processors being configured to:
    (a) receive an input comprising information pertaining to a genetic variant of unknown significance (VUS);
    (b) retrieve the reference genotype data of the plurality of reference individuals from the one or more databases, wherein
the reference genotype data comprises a haplotype graph having a computer data structure of a Directed Acyclic Graph (DAG),
the DAG comprises nodes and directed edges each connecting an initial node and a terminating node, each node representing a genotype of a genetic marker, each directed edge indicating a probability of observing the terminating node given the initial node, the nodes and directed edges of the DAG being obtained from densely sequenced reference data of the plurality of reference individuals, and
the densely sequenced reference data of the plurality of reference individuals comprise genotype data at a genetic locus corresponding to the VUS; and
(c) perform statistical imputation on the sparsely sequenced genotype data of the plurality of candidate individuals, thereby obtaining imputed genotype data with reference to the VUS for the plurality of candidate individuals,
wherein
performing statistical imputation comprises applying the sparsely sequenced genotype data of the plurality of candidate individuals to the haplotype graph to obtain the imputed genotype data with reference to the VUS for the plurality of candidate individuals, and
the genetic locus corresponding to the VUS for the plurality of candidate individuals is not directly assayed by a genotyping chip or a genotyping platform.

17. The system of claim 16, wherein the plurality of reference individuals comprises 1,000 or more individuals.

18. A genetic information processing system, comprising:
computer memory storing one or more databases comprising reference genotype data of a plurality of reference individuals and sparsely sequenced genotype data and phenotype data of a plurality of candidate individuals; and
one or more computer processors coupled to the computer memory, the one or more processors being configured to:

(a) receive an input comprising information pertaining to a genetic variant of unknown significance (VUS);
(b) retrieve the reference genotype data of the plurality of reference individuals from the one or more databases,
wherein
the reference genotype data comprises one or more hash tables,
each hash table is a computer data structure that maps words to values,
each of the words comprises one or more genetic markers,
each hash table is obtained using densely sequenced reference data of the plurality of reference individuals,
the densely sequenced reference data of the plurality of reference individuals comprise genotype data at a genetic locus corresponding to the VUS; and
(c) perform Identity by Descent (IBD)-based imputation on the sparsely sequenced genotype data of the plurality of candidate individuals, thereby obtaining imputed genotype data with reference to the VUS for the plurality of candidate individuals,
wherein
performing IBD-based imputation comprises looking up words obtained from the sparsely sequenced genotype data of the plurality of candidate individuals in the one or more hash tables to obtain the imputed genotype data with reference to the VUS for the plurality of candidate individuals, and
the genetic locus corresponding to the VUS for the plurality of candidate individuals is not directly assayed by a genotyping chip or a genotyping platform.

19. The system of claim 18, wherein the plurality of reference individuals comprises 1,000 or more individuals.

20. The system of claim 1, wherein the reference genotype data comprise a haplotype graph having a computer data structure of a DAG, genotype data stored in one or more hash tables, opposite homozygous data, or any combinations thereof.

* * * * *